(12) United States Patent
Dobbs

(10) Patent No.: US 8,545,766 B2
(45) Date of Patent: *Oct. 1, 2013

(54) COUNTERFEIT DETECTOR PEN

(71) Applicant: Mark Dobbs, Port Washington, NY (US)

(72) Inventor: Mark Dobbs, Port Washington, NY (US)

(73) Assignee: Dri-Mark Products, Port Washington, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/684,360

(22) Filed: Nov. 23, 2012

(65) Prior Publication Data

US 2013/0078162 A1    Mar. 28, 2013

Related U.S. Application Data

(63) Continuation of application No. 12/348,398, filed on Jan. 5, 2009, now Pat. No. 8,406,499.

(51) Int. Cl.
*G06K 9/22*    (2006.01)

(52) U.S. Cl.
USPC ........ 422/405; 422/82.05; 422/401; 422/430; 382/135; 436/164; 436/165; 162/140

(58) Field of Classification Search
USPC ................ 382/135; 436/164, 165; 162/140; 422/82.05, 401, 405, 430
See application file for complete search history.

(56) References Cited

U.S. PATENT DOCUMENTS 5,063,163 A * 11/1991 Carmeli ..................... 436/94
8,406,499 B2 * 3/2013 Dobbs ....................... 382/135

* cited by examiner

*Primary Examiner* — Lyle Alexander
(74) *Attorney, Agent, or Firm* — Ostrolenk Faber LLP

(57) ABSTRACT

A counterfeit currency detector including a tubular body having a forward end and a rearward end, a contact assembly mounted at the forward end of the tubular body, and a counterfeit solution applicator mounted at the rearward end of the tubular body. The contact assembly includes an ultraviolet light source.

10 Claims, 1 Drawing Sheet

COUNTERFEIT DETECTOR PEN

The present application is a continuation of U.S. patent application Ser. No. 12/348,398, filed Jan. 5, 2009 in the name of Mark DOBBS, and entitled COUNTERFEIT DETECTOR PEN, which claims benefit of and priority to U.S. provisional Patent Application Ser. No. 61/097,132 filed Sep. 15, 2008 entitled COUNTERFEIT DETECTOR PEN, the entire content of each of which is hereby incorporated by reference herein.

BACKGROUND

The present invention relates to an apparatus for detecting counterfeit paper currency.

Ever since the paper currency was invented and put into use, the governments throughout the world have been concerned with the problem of counterfeiting. As the duplicating and printing, and especially the photocopying technologies have advanced over the years, it is more difficult than ever to distinguish between a counterfeit and a legitimate paper currency. The problem of counterfeiting paper currency is and has been a major concern of many governments around the world.

In response to the ever-growing concern of counterfeiting, devices have been developed for detecting counterfeit currency. For example, U.S. Pat. No. 5,063,163 discloses a method of detecting counterfeit paper currency where a test solution having an initial color is applied to an area of a paper currency to be tested. After waiting for a predetermined time period, the color of the test area is compared with a predetermined standard to determine if a reaction has taken place. If the tested currency is a counterfeit paper currency, the test solution changes its color from the initial color to a black coloration. Even though the above solution is relatively simple, it is not always reliable.

Recently, another counterfeit detecting solution has been introduced, as described in U.S. Pat. No. 6,714,288. Paper currency now includes a polymer thread, which is embedded vertically in the paper to the right of the portrait and indicates the currency's denomination. This thread glows orange when held under an ultraviolet light. The '288 patent discloses an apparatus incorporating an ultraviolet lamp for currency examination. Unfortunately, such conventional devices utilizing ultraviolet lamps are expensive to manufacture, and in most cases, are rather bulky and complex in design.

Therefore, there is a need in the art for a simple apparatus for detecting counterfeit currency.

SUMMARY

According to a general example of the present invention, there is provided a counterfeit currency detector including a tubular body having a forward end and a rearward end, a contact assembly mounted at the forward end of the tubular body, and a counterfeit solution applicator mounted at the rearward end of the tubular body. The contact assembly includes an ultraviolet light source.

The above features of the invention will be more readily apparent from the description of the preferred embodiments thereof taken in conjunction with the accompanying drawings and appended claims.

BRIEF DESCRIPTION OF THE DRAWINGS

The invention is illustrated by way of example and not limitation and the figures of the accompanying drawings in which like references denote like or corresponding parts, and in which.

DETAILED DESCRIPTION OF THE INVENTION

Figure 1:
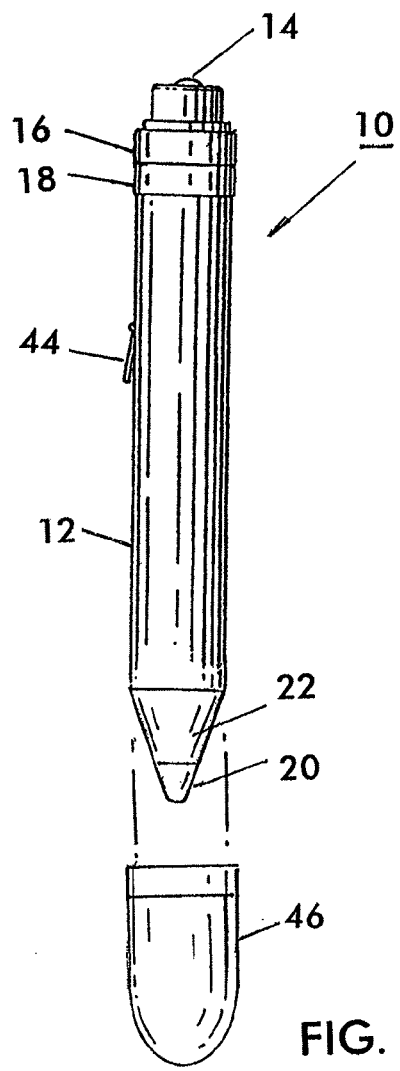
FIG. 1 is a front view of the counterfeit detector pen showing a mounted ultraviolet light source and a counterfeit solution applicator.

With reference to FIG. 1, there is shown a counterfeit detector pen 10 which generally includes a tubular body 12 having an ultraviolet light source 14, mounted in a contact assembly 16 at the forward end 18 of the tubular body 12, and a counterfeit solution applicator 20 mounted at the rearward end 22 of the tubular body 12. A cap 46 may be secured over the rearward end 22 to protect the applicator 20.

Figure 3:
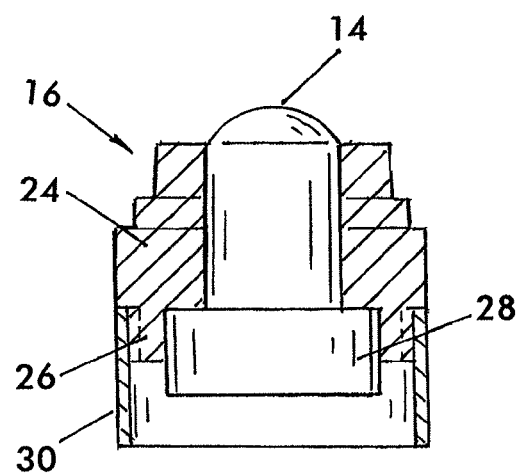
FIG. 3 is a cross-sectional view of the contact assembly.
Figure 2:
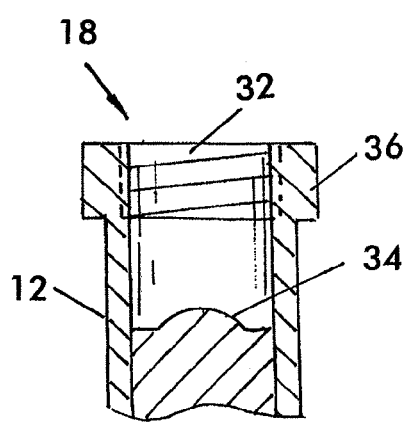
FIG. 2 is a cross-sectional view of the forward end of the counterfeit detector pen.

As shown in FIG. 3, the contact assembly 16 preferably includes a rotatable skirt 24 having a threaded end 26, the ultraviolet light source 14, a battery 28, both fixedly positioned within the rotatable skirt 24, and a biasing element 30 attached to the threaded end 26 of the rotatable skirt 24. As shown in FIG. 2, the forward end 18 of the tubular body 12 is a first hollow cylindrical tube 36 with an inner threading 32. A protruding switch 34 is fixedly secured within the first hollow cylindrical tube 36. To secure the contact assembly 16 within the forward end 18, the threaded end 26 of the rotatable skirt 24 is screwed into the inner threaded surface 32. Further rotation of the rotatable skirt 24 relative to the tubular body 12 completes the electrical circuit of the ultraviolet light source by connecting the protruding switch 34 to the battery 28 to turn the ultraviolet light source 14 ON. Rotation of the skirt 24 in the opposite direction disconnects the battery from the protruding switch and turns the ultraviolet light source 14 OFF.

In use, to detect a counterfeit currency, a user will rotate the skirt 24 to turn the ultraviolet light source 14 ON and will flash the ultraviolet light onto the tested currency. If the tested currency is real the embedded vertical polymer thread will glow orange under the ultraviolet light.

Throughout this written description and the following claims, the terms "forward," "front" and similar terms refer to the end of counterfeit detector pen 10 where the ultraviolet light source is mounted, and the terms "rearward," "rear" and the like refer to the opposite end where the counterfeit solution applicator is mounted.

Figure 4:
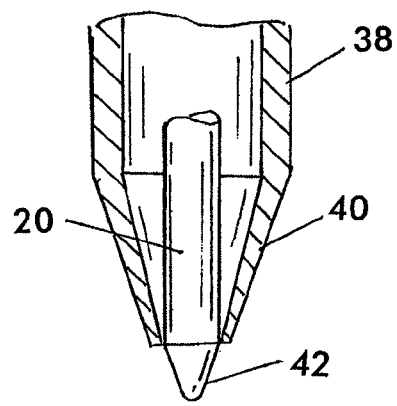
FIG. 4 is a cross-sectional view of the rearward end of the counterfeit detector pen.

The rearward portion of the counterfeit detector pen 10 includes a second hollow cylindrical tube 38 shown in more detail in FIG. 4. Diameter of the second cylindrical tube 38 is preferably smaller than the diameter of the first cylindrical tube 36. Further, the second cylindrical tube 38 preferably includes a tapered end 40 into which the counterfeit solution applicator 20 is inserted to be secured therein. Applicator 20 is impregnated with a test solution, which can be applied to the currency to be tested using an applicator's tip 42. Alternatively, the applicator 20 may include a reservoir filled with the test solution and connected to the applicator's tip 42. Test solution preferably detects the content of starch in the currency paper. However, any other known test solution may be utilized.

In use, to detect counterfeit paper currency, a user will generally apply the test solution to the tested currency using the tip of the applicator 20. The preferred solution, which is light golden-brown in color, when applied to a counterfeit paper currency, forms a bluish-black complex with starch. On the other hand, the color of the preferred test solution does not change in the case of a genuine paper currency.

The test solution is preferably a reagent solution described in U.S. Pat. No. 5,063,163. Specifically, the reagent solution preferably contains iodine and a suitable solvent, preferably selected from the group consisting of alcohol, carbon disulfide, chloroform, ether, carbon tetrachloride, glycerol, and an alkaline iodide solution. The alkaline iodide may preferably be selected from the group consisting of sodium iodide and potassium iodide. In particular, the light golden-brown test solution contains about 0.5% to about 2.0% iodine, about 48.0% to about 49.5% water, and about 44% to about 50% alcohol by volume of the reagent solution. The solution may also contain up to about 6% of a bleaching agent, such as hydrogen peroxide, by volume of the solution. It should be noted that various percentages of the noted ingredients may be altered in order to provide various test solutions of varying strengths. The main component of the test solution is the iodine element. Other types of iodine solutions suitable for the described purpose may also be used with the described counterfeit detector pen.

The counterfeit detector pen 10 is approximately the same size as a pen, and may be easily carried in a purse or a pocket. A clip 44 may be secured to the outer surface of the tubular body 12 to enable a user to carry the counterfeit detector pen in a pocket.

As described above, the invention improves and facilitates the detection of paper currency counterfeits, by providing dual mode of testing for counterfeiting. In use, one would use the pen shaped device of the present invention and quickly test whether the paper of which the currency is made is the more expensive starch based paper used for currency. Even if that test passes, one can test using the ultraviolet light facility to test whether the currency passes the second' test. Alternatively, one can start with the ultraviolet test and then proceed to the iodine test. In novel fashion, the present invention provides a pen like device with two modes of testing, unlike the currency counterfeiting testing apparatus of the prior art.

Many different embodiments of the present invention may be constructed without departing from the spirit and scope of the invention. It should be understood that the present invention is not limited to the specific embodiments described in this specification. To the contrary, the present invention is intended to cover various modifications and equivalent arrangements included within the spirit and the scope of the claims.

What is claimed is:

1. A counterfeit currency detector, comprising:
    a pen-shaped and tubular detector body having a forward end and a rearward end and a middle body by which the detector is configured to be held by in a user's hand;
    an ultraviolet light source assembly including an ultraviolet light source mounted at one end of the detector body;
    a counterfeit solution applicator comprising at least the middle body of the detector body, to enable the user to use either or both of the ultraviolet light source assembly and the solution applicator to test currency;
    wherein the counterfeit solution applicator is impregnated with a test solution configured to change color when applied to a counterfeit currency;
    wherein the ultraviolet light source is configured to be turned on to flash ultraviolet light onto a currency note to be tested to cause a thread in the currency note to glow under the ultraviolet light.

2. The counterfeit currency detector according to claim 1, further including a contact assembly which is configured to connect the ultraviolet light source assembly to the detector body.

3. The counterfeit currency detector according to claim 2, wherein the contact assembly comprises a rotatable skirt, the ultraviolet light source assembly being fixedly mounted within the rotatable skirt.

4. The counterfeit currency detector according to claim 3, wherein the rotatable skirt of the contact assembly is rotatably insertable into the forward end of the detector body.

5. The counterfeit currency detector according to claim 2, wherein the contact assembly further comprises a battery.

6. The counterfeit currency detector according to claim 5, wherein the detector body comprises a switch and wherein the rotatable skirt is selectively rotatable to bring the battery in contact with the switch closing an electrical circuit of the ultraviolet light source to turn the ultraviolet light source on.

7. The counterfeit currency detector according to claim 1, wherein the detector body is cylindrical.

8. The counterfeit currency detector according to claim 1, wherein the solution includes iodine and a solvent selected from the group consisting of alcohol, carbon disulfide, chloroform, ether, carbon tetrachloride and glycerol.

9. The counterfeit currency detector according to claim 1, wherein the test solution contains about 0.5% to about 2.0% iodine, about 48.0% to about 49.5% water, and about 44% to about 50% alcohol by volume of the solution.

10. The counterfeit currency detector according to claim 9, further including about 6% of a bleaching agent.

\* \* \* \* \*